(12) United States Patent
Nambakam et al.

(10) Patent No.: US 12,396,628 B2
(45) Date of Patent: Aug. 26, 2025

(54) VISUALIZATION SYSTEM WITH REAL-TIME IMAGING FUNCTION

(71) Applicant: VITAVIEW MEDTECH (ZHEJIANG) CO., LTD., Ningbo (CN)

(72) Inventors: Vasudev Nambakam, Ningbo (CN); Yan Peng Ng, Ningbo (CN); Jianan Li, Ningbo (CN)

(73) Assignee: Vitaview Medtech (Zhejiang) Co., LTD., Ningbo (CN)

( * ) Notice: Subject to any disclaimer, the term of this patent is extended or adjusted under 35 U.S.C. 154(b) by 415 days.

(21) Appl. No.: 17/999,609

(22) PCT Filed: May 12, 2021

(86) PCT No.: PCT/CN2021/093461
§ 371 (c)(1),
(2) Date: Nov. 22, 2022

(87) PCT Pub. No.: WO2021/238661
PCT Pub. Date: Dec. 2, 2021

(65) Prior Publication Data
US 2023/0190083 A1    Jun. 22, 2023

(30) Foreign Application Priority Data

May 28, 2020  (CN) .......................... 202010470740.7

(51) Int. Cl.
*A61B 1/04*    (2006.01)
*A61B 1/06*    (2006.01)
*A61B 1/00*    (2006.01)

(52) U.S. Cl.
CPC ............ *A61B 1/043* (2013.01); *A61B 1/0638* (2013.01); *A61B 1/00186* (2013.01)

(58) Field of Classification Search
CPC ................................ A61B 1/046; H04N 25/13
See application file for complete search history.

(56) References Cited

U.S. PATENT DOCUMENTS 4,607,007 A * 8/1986 Lanier .............. G01N 33/56972
  435/973
6,331,156 B1 * 12/2001 Haefele .................... A61B 1/07
  600/179

(Continued)

*Primary Examiner* — Anh Tuan T Nguyen
*Assistant Examiner* — Jae Woo
(74) *Attorney, Agent, or Firm* — Clement Cheng

(57) ABSTRACT

The invention discloses a visualization system with a real-time imaging function, comprising: a receiving end, a light source, an imaging system, and a display device. The light source comprises a red light source and a fluorescence excitation light source; the imaging system comprises a red light image sensor and a fluorescence image sensor to process a signal to output a real-time visualization signal to the display device. Through the technical scheme, the visualization system can provide sufficient background information and obtain a clear and complete real-time image for a surgeon only by using a specific band of red light to illuminate a surgical scene, the visualization system is simple in whole structure, is convenient in a control method, is simple and highly effective in the imaging process procedure, has a good use experience while the manufacturing and maintenance costs are low, and has a very high applicability and popularization.

13 Claims, 1 Drawing Sheet

(56) References Cited

U.S. PATENT DOCUMENTS

| | | | | |
|---|---|---|---|---|
| 10,477,119 | B2* | 11/2019 | Shigeta | H04N 23/11 |
| 10,779,734 | B2* | 9/2020 | Fengler | A61B 5/0062 |
| 11,788,966 | B2* | 10/2023 | Ikenaga | A61B 1/0655 |
| | | | | 600/407 |
| 2002/0035330 | A1* | 3/2002 | Cline | A61B 1/045 |
| | | | | 600/478 |
| 2002/0147383 | A1* | 10/2002 | Weber | A61B 5/0084 |
| | | | | 600/109 |
| 2011/0270057 | A1* | 11/2011 | Pascal | A61B 1/0655 |
| | | | | 600/317 |
| 2013/0274596 | A1* | 10/2013 | Azizian | A61B 5/0071 |
| | | | | 600/424 |
| 2014/0194748 | A1* | 7/2014 | Yamamoto | A61B 5/489 |
| | | | | 600/473 |
| 2015/0262383 | A1* | 9/2015 | Yajko | G06V 10/56 |
| | | | | 382/108 |
| 2015/0381909 | A1* | 12/2015 | Butte | A61B 1/00045 |
| | | | | 250/578.1 |
| 2016/0062103 | A1* | 3/2016 | Yang | A61B 1/07 |
| | | | | 250/552 |
| 2017/0209050 | A1* | 7/2017 | Fengler | G01J 3/10 |
| 2017/0273567 | A1* | 9/2017 | Fengler | A61B 1/0655 |
| 2018/0210188 | A1* | 7/2018 | Ganapati | A61B 1/0638 |
| 2018/0228347 | A1* | 8/2018 | Yamamoto | A61B 1/00057 |
| 2020/0196846 | A1* | 6/2020 | Themelis | G02B 21/0012 |
| 2020/0380735 | A1* | 12/2020 | Birbaumer | G09G 5/026 |
| 2021/0106214 | A1* | 4/2021 | Zhang | A61B 5/7221 |
| 2021/0294084 | A1* | 9/2021 | Yamaguchi | A61B 1/000095 |
| 2024/0268647 | A1* | 8/2024 | Holthaus | A61B 1/00186 |

* cited by examiner

VISUALIZATION SYSTEM WITH REAL-TIME IMAGING FUNCTION

BACKGROUND OF THE INVENTION

1. Field of the Invention

The invention relates to the field of medical devices, and more particularly, to a visualization system with a real-time imaging function.

2. Description of the Related Art

In the prior art, a fluorescent navigation endoscope is a new type of operation image acquiring technology in which a specific near-infrared fluorescent contrast agent is injected, an imaging area is illuminated by using two light sources, that is, a white light and an excitation light, and a clear colorful image of the imaging area and a fluorescence image reflective of lesion information are obtained. The prior art usually adopts 1-Chip RGB system or 3-Chip RGB system to generate white light image for analyzing the background. The 1-Chip RGB system is not able to capture and process a white signal and a fluorescence signal simultaneously, so time division multiplexing is added therein. In order to obtain a better imaging result, a light source management system is quite complex, so as to alternately turn on/off the white light source and the fluorescence excitation light source at a high synchronous frequency (e.g., 50 Hz or 60 Hz). The 3-Chip RGB system uses 3 sensors to detect RGB signals reflected by the RGB channel. In this case, the red sensor is also used to detect the NIR signal. To avoid turning the light source on/off frequently, in such architectures, the red light is turned off at all times. Only green and blue light is used and the image acquired from the green and blue sensors is used to create the background image. In such architectures, as the band of red light cannot be collected, some tissues may not be well differentiated in the background image. As a result, it may either fail to capture certain types of anatomy within the human body, or provide excessive background information to the surgeon that causes confusion, or even excess excision. It is therefore necessary to provide an improved visualization system, which is intended to avoid the above-mentioned potential imaging problems while greatly simplifying the image processing and the light source excitation process. It enables simple daily usage and relevant maintenance, so that the new visualization technology can be widely used in a variety of applications.

SUMMARY OF THE INVENTION

Given that the foregoing problems exist in the prior art, the present invention provides a visualization system with a real-time imaging function.

The technical solution is as follows:
a visualization system with a real-time imaging function, comprising:
a receiving end comprising a camera interface and a light guide interface;
a light source, connected to the light guide interface through a light guide, and configured to successively provide an imaging light source for the receiving end, the light source comprising a first light source and a second light source, the first light source emitting fluorescence excitation light, and the second light source emitting red light;
an imaging system, connected to the camera interface through a light guide connector, and configured to acquire a fluorescence imaging signal and a red imaging signal, respectively, according to a light reflected from the imaging light source successively received by the receiving end so as to output a real-time visualization image; and
a display device, electrically connected to the imaging system, and configured to display the real-time visualization image.

Preferably, in the visualization system, wherein the imaging system comprises a camera group and a camera controller;
wherein, the camera group is configured to successively collect and filter the light reflected from the imaging light source to output a corresponding fluorescence image and a red light image;
the camera controller is connected to the camera group through camera cables, and outputs the corresponding fluorescence imaging signal and the red imaging signal according to the fluorescence image and the red image respectively.

Preferably, in the visualization system, wherein the camera controller is further electrically connected to the light source;
the camera controller generates a corresponding light source instruction according to a user instruction in the exterior, and the light source turns on or off the first light source and/or the second light source according to the light source instruction.

Preferably, in the visualization system, wherein the camera group comprises a fluorescence image sensor and a red light image sensor;
the fluorescence image sensor comprises a fluorescence filter for filtering all the other light of the light reflected from the imaging light except a wavelength band of fluorescence corresponding to the fluorescence excitation light, the light reflected from the imaging light generates the fluorescence image in the fluorescence image sensor through the fluorescence filter;
the red light image sensor comprises a red light filter for filtering all the other light reflected from the imaging light except a wavelength band corresponding to the red light, the light reflected from the imaging light generates the red light image in the red light image sensor through the red light filter.

Preferably, in the visualization system, wherein the fluorescence image sensor and the red light image sensor are arranged in the same device and are spatially interleaved.

Preferably, in the visualization system, wherein the camera controller further comprises an image enhancement unit;
the image enhancement unit performs image enhancement on the fluorescence image and the red image using non-linear histogram equalization, and outputs the fluorescence imaging signal and the red light imaging signal according to an image enhancement result.

Preferably, in the visualization system, the image enhancement unit includes spatial filtering mechanisms which functions to reduce medium-low spatial frequency signals in the red light signal and increase the medium-high spatial frequency signals in the red light signal. Further, the image enhancement unit includes an inversion function, wherein the higher signal levels at the input are mapped to a lower signal level at the output and vice-versa.

Preferably, in the visualization system, wherein the camera controller further comprises a light source controller;

the light source controller is configured to determine whether a sufficient light incoming amount of the light reflected from the imaging light source, collected by the camera group, is provided, according to a preset standard, and to control the light source to supplement light when the amount of incoming light is not sufficient.

Preferably, in the visualization system, wherein the imaging device displays the real-time visualization image by using a RGB color mode; wherein, a RGB red channel is determined by the red light image signal;

a RGB green channel is determined by a superposition of the red light image signal and the fluorescence image signal; and a RGB blue channel is determined by the red light image signal.

Preferably, in the visualization system, wherein a band for the red light emitted from the second light source is in a range of 600 nm to 700 nm.

Preferably, in the visualization system, wherein a band for the fluorescence excitation light emitting from the first light source is in a range of 780 nm to 820 nm, to excite the ICG dye.

Preferably, in the visualization system, wherein a band for the fluorescence excitation light emitting from the first light source is in a range of 480 nm to 520 nm, to excite the fluorescein dye.

Preferably, in the visualization system, wherein the receiving end is an endoscope.

Preferably, in the visualization system, wherein the receiving end is an optical coupling system for use in open surgery when the visualization system is used for open surgery.

By adopting the above-mentioned technical solutions, the present invention has the beneficial effects. Through the technical scheme, the visualization system can provide sufficient background information and obtain a clear and complete real-time image for a surgeon only by using a specific band of red light to illuminate a surgical scene, the visualization system is simple in whole structure, is convenient in a control method, is simple and highly effective in the imaging process procedure, has a good use experience while the manufacturing and maintenance costs are low, and has a very high applicability and popularization.

DETAILED DESCRIPTION

The technical solutions in the embodiments of the present invention will be clearly and completely described below with reference to the accompanying drawings in the embodiments of the present invention. Obviously, the described embodiments are only a part of the embodiments of the present invention, but not all of the embodiments. Based on the embodiments of the present invention, all other embodiments obtained by those of ordinary skill in the art without creative work fall within the protection scope of the present invention.

It should be noted that the embodiments of the present invention and the features of the embodiments may be combined with each other under the condition of no conflict.

The present invention will be further described below with reference to the accompanying drawings and specific embodiments, but it is not intended to limit the present invention.

Given that the foregoing problems exist in the prior art, the present invention provides a visualization system with a real-time imaging function.

The technical solution is as follows.

Figure 1:
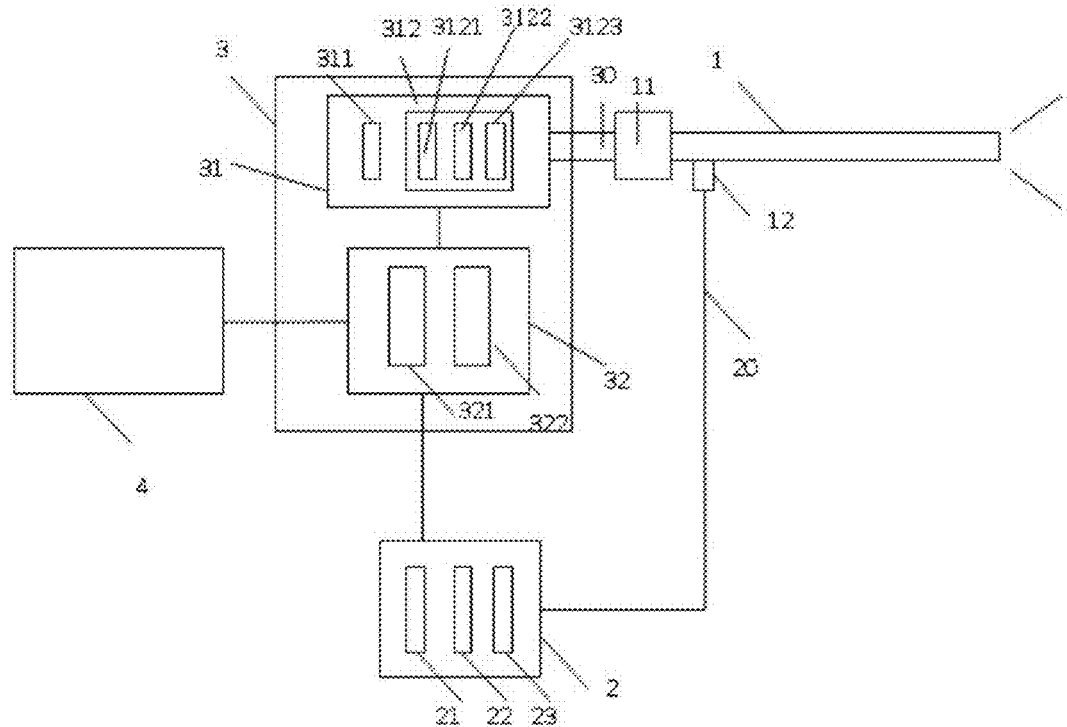
FIG. 1 shows a schematic diagram of a structure of a visualization system with a real-time imaging function according to the present invention.

Referring to FIG. 1, a visualization system with a real-time imaging function, comprising:

a receiving end 1 comprising a camera interface 11 and an optical fiber interface 12;

a light source 2, connected to the light guide interface 12 through a light guide 20, and configured to successively provide an imaging light source for the receiving end 1, the light source 2 comprising a first light source 21, and a second light source 22, the first light source 21 emitting fluorescence excitation light, and the second light source 22 emitting red light;

an imaging system 3, connected to the camera interface 11 through a light guide connector 30, configured to acquire a fluorescence imaging signal and a red imaging signal, respectively, according to a light reflected from the imaging light source successively received by the receiving end 1, so as to output a real-time visualization image;

a display device 4, electrically connected to the imaging system 3, and configured to display the real-time visualization image.

As a preferred embodiment, in the visualization system, wherein the receiving end is an endoscope.

As a preferred embodiment, in the visualization system, wherein the receiving end is an optical coupling system for use in open surgery when the visualization system is used for open surgery.

In a preferred embodiment of the present invention, the receiving end in the visualization system can be flexibly configured into an endoscope with camera interface and light guide interface or an open optical coupling system for open surgery according to the actual needs of the surgery. It can be flexibly deployed according to different surgical needs, which enhances the application scope of the visualization system.

As a preferred embodiment, in the visualization system, wherein the imaging system 3 comprises a camera group 31 and a camera controller 32;

wherein, the camera group 31 is configured to successively collect and filter the light reflected from the imaging light source to output a corresponding fluorescence image and a red light image;

wherein, the camera assembly 31 is configured to successively collect and filter the light coming from the light guide connector 30 through an array of image sensors configured to detect the fluorescence imaging signal and the red light imaging signal, and output a corresponding fluorescence image and a red light image;

the camera controller 32 is connected to the camera group 31 through camera cables, and outputs the corresponding fluorescence imaging signal and the red light imaging signal according to the fluorescence image and the red light image.

As a preferred embodiment, in the visualization system, wherein the camera controller 32 is also electrically connected to the light source 2;

the camera controller 32 generates a corresponding light source instruction according to a user instruction in the exterior, and the light source 2 turns on or off the first light source 21 and/or the second light source 22, and/or the third light source 23 according to the light source instruction.

In a preferred embodiment of the present invention, wherein the light source 2 comprises a third light source 23, the third light source 23 emits white light.

As a preferred embodiment, in the visualization system, wherein the camera group 31 comprises a fluorescence image sensor 312 and a red light image sensor 311;

the fluorescence image sensor 312 comprises a plurality of sub image sensors 3121, 3122, 3123 which are configured to optionally receive light with different wavelengths. The sub image sensor 3121 receives blue light, the sub image sensor 3122 receives green light and the sub image sensor 3123 receives near infrared light;

the red image sensor 311 is configured to receive red light.

In a preferred embodiment of the present invention, the camera group 31 comprises a fluorescence image sensor and a red light image sensor. The fluorescence image sensor is used to collect the fluorescence reflected from the fluorescence excitation light through a filter lens and generates a fluorescence image. Since the fluorescence is only produced in a specific area where contrast agents work as desired under the influence of the fluorescence excitation light, the above-mentioned fluorescence image represents an area of interest to a surgeon; similarly, the red light image sensor is used to collect the light reflected from the red light through the filter lens and generates a red light image which represents the background context. Since human tissue provides significant reflection in the "red" spectral range during a surgical procedure, it makes a good background information for surgical context by simply using the red light as a light source for the background.

As a preferred embodiment, in the visualization system, wherein the fluorescence image sensor and the red light image sensor are arranged in the same device and are spatially interleaved.

As a preferred embodiment, in the visualization system, wherein the camera controller 32 further comprises an image enhancement unit 321;

the image enhancement unit 321 performs image enhancement on the fluorescence image and the red light image using non-linear histogram equalization, and outputs the fluorescence imaging signal and the red light imaging signal according to an image enhancement result.

In a further preferred embodiment of the present invention, performing image enhancement on the obtained fluorescence image and the red light image by using non-linear mapping technique, so that images can be clearly presented to the surgeon, and the user experience is improved. The image enhancement unit includes spatial filtering mechanisms which functions to reduce low spatial frequency signals in the red signal and increase the high spatial frequency signals in the red signal. Further, the image enhancement unit may include an inversion function, wherein the higher signal level at the input is mapped to a lower signal level at the output and vice-versa.

As a preferred embodiment, in the visualization system, wherein the camera controller 32 further comprises a light source controller 322;

the light source controller 322 is configured to determine whether a sufficient light incoming amount of the light reflected from the imaging light source, collected by the camera group, is provided according to a preset standard, and to control the light source to supplement light when the light incoming amount is not sufficient.

In a further preferred embodiment of the present invention, the camera controller 32 also has an automatic light supplementing function. More specifically, the camera controller 32 can determine whether the light incoming amount is too low based on parameters of the returned image, such as the brightness, sharpness, and contrast. In addition, when it is determined that the light incoming amount is too low, the camera controller 32 may control the light source to supplement light again.

As a preferred embodiment, in the visualization system, wherein the display device 4 displays the real-time visualization image by using a RGB color mode; wherein, a RGB red channel is determined by the red light image signal;

a RGB green channel is determined by a superposition of the red light image signal and the fluorescence image signal; and a RGB blue channel is determined by the red light image signal.

In a further preferred embodiment of the present invention, when it is desired to present images to be observed in real time, both the RGB red channel and the RGB blue channel are unified presented by directly using the red light image signal, and the RGB green channel is present simply by a superposition of the red light image signal and the fluorescence image signal. As an end result, the display device 4 will present the background area corresponding to the red channel and the blue channel to be in grey level, so as to emphasize the green area, so that the surgeon better visualizes the anatomy.

As a preferred embodiment, in the visualization system, wherein a band for the red light emitting from the second light source 22 is in a range of 600 nm to 700 nm.

In a further preferred embodiment of the present invention, the visualization system provided in the present invention is also suitable for use in a 4-Chip RGB system for achieving a better imaging result. In particular, the 4-Chip RGB system comprises a red light image sensor 311, a green light image sensor 3121, a blue light image sensor 3122 and a NIR image sensor 3123. In this case, the light source is a fluorescence excitation light source 21, a red light source 22, and a white light source 23. The band of the red light source 22 is in a range of 600 nm to 700 nm. Due to the fact that the commonly used band of the white light source is mainly in the range of 400 nm to 700 nm, and it may attenuate swiftly after going beyond 600 nm, the band of the red light source 22 needs to be supplemented for the white light source 23 accordingly. The advantage of this is that human tissue or blood in the red light spectrum has very important information, such as the location of blood vessels, etc., which can provide good background environment when surgeons perform surgery such as resection.

Figure 2:
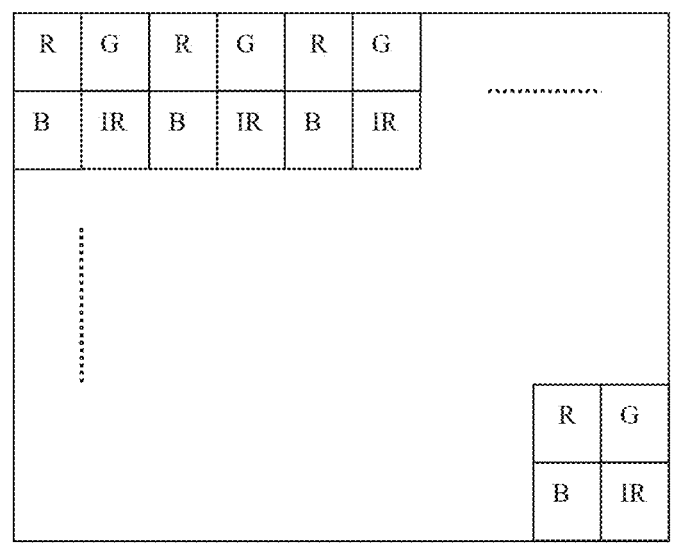
FIG. 2 shows a filtering mode in a 1-chip RGB infrared imaging system in a visualization system with a real-time imaging function of the present invention.

In a further preferred embodiment of the present invention, the visualization system provided in the present invention is also suitable for use in a 1-Chip RGB infrared imaging system for achieving a better imaging result. In particular, the 1-Chip RGBIR system comprises a single CMOS image sensor with an exemplary filter pattern as shown in FIG. 2. The light source thereof is similar to the one described hereinbefore.

As a preferred embodiment, in the visualization system, wherein a band for the fluorescence excitation light emitting from the first light source 21 is in a range of 800 nm to 820 nm.

In a further preferred embodiment of the present invention, the band of the fluorescence excitation light emitting from the first light source 21 is defined in the range of 800 nm to 820 nm. In order to collect fluorescence obtained from the excitation of the fluorescence excitation light, the band of the fluorescence received by the corresponding fluorescence image sensor is set to be in the range of 820 nm to 840 nm to capture the fluoresced image.

As a preferred embodiment, in the visualization system, wherein a band of the fluorescence excitation light emitting from the first light source 21 is in a range of 480 nm to 500 nm, to excite a specific contrast agent, e.g., fluorescein.

In a further preferred embodiment of the present invention, the band of the fluorescence excitation light emitting from the first light source 21 is defined in the range of 480 nm to 500 nm. In order to collect fluorescence obtained from the excitation of the fluorescence excitation light, the band of the fluorescence received by the corresponding fluorescence image sensor is set to be in the range of 500 nm to 520 nm to capture the fluoresced light.

A particular embodiment is provided now for better illustrate the technical solution:

In this particular embodiment of the present invention, the camera controller and the display are integrated into a personal computer with a display screen. The personal computer is connected to the camera group and the light source. The surgeon performs the following procedures before performing the surgery: sending an instruction via a relevant program in the personal computer to the light sources, so as to simultaneously turn on the red light source and the fluorescence excitation light source, the receiving end is coupled through a light guide to illuminate an surgical area, and the surgery area is excited to emit a fluorescence signal, and other background area will reflect red light; the camera group collects the reflected light and filters the collected light through a filter, to output a fluorescence image and a red light image to the camera controller; the camera controller determines, according to a preset comparison table for light incoming amount, whether the light incoming amount is too low based on parameters of the returned image, such as the brightness, sharpness, contrast, if it is determined that the light incoming amount is too low, the camera controller may control the light source to supplement light again; if not, performing image enhancement on the obtained images by using non-linear mapping technique, and the processed images are presented on the display screen in real time; the presented images are processed in a RGB color mode; the red channel, the blue channel are directly determined by the red light image signal and the channels are all the same, forming the background; the green channel is determined by a further superposition of the red light image signal with the fluorescence image signal, representing the surgical area of interest; then the background is treated as a gray level so as to remove the color thereof, so that a real-time image with high contrast is obtained, help the surgeon performing the surgical operation smoothly.

In conclusion, through the technical scheme, the visualization system can provide sufficient background information and obtain a clear and complete real-time image for a surgeon only by using a specific band of red light to illuminate a surgical scene, the visualization system is simple in whole structure, is convenient in a control method, is simple and highly effective in the imaging process procedure, has a good use experience while the manufacturing and maintenance costs are low, and has a very high applicability and popularization.

The above descriptions are only the preferred embodiments of the invention, not thus limiting the embodiments and scope of the invention. Those skilled in the art should be able to realize that the schemes obtained from the content of specification and drawings of the invention are within the scope of the invention.

What is claimed is:

1. A visualization system with a real-time imaging function, comprising:
   a receiving end comprising a camera interface and a light guide interface;
   a light source, connected to the light guide interface through a light guide, and configured to successively provide an imaging light source for the receiving end, the light source comprising a first light source and a second light source, the first light source emitting fluorescence excitation light, and the second light source emitting red light;
   an imaging system, connected to the camera interface through a light guide connector, and configured to acquire a fluorescence imaging signal and a red imaging signal, respectively, according to a light reflected from the imaging light source successively received by the receiving end so as to output a real-time visualization image; and
   a display device, electrically connected to the imaging system, and configured to display the real-time visualization image,
   wherein the imaging device displays the real-time visualization image by using a RGB color mode; wherein,
   a RGB red channel is determined by the red light image signal;
   a RGB green channel is determined by a superposition of the red light image signal and the fluorescence image signal; and
   a RGB blue channel is determined by the red light image signal.

2. The visualization system of claim 1, wherein the imaging system comprises a camera group and a camera controller;
   wherein, the camera group is configured to successively collect and filter the light reflected from the imaging light source to output a corresponding fluorescence image and a red light image;
   the camera controller is connected to the camera group through camera cables, and outputs the corresponding fluorescence imaging signal and the red light imaging signal according to the fluorescence image and the red light image.

3. The visualization system of claim 2, wherein the camera controller is further electrically connected to the light source, the light source comprises a third light source, the third light source emits white light;
   the camera controller generates a corresponding light source instruction according to a user instruction, and the light source turns on or off the first light source and/or the second light source and/or the third light source according to the light source instruction.

4. The visualization system of claim 3, wherein the camera controller further comprises a light source controller;
   the light source controller is configured to determine whether a sufficient light incoming amount of the light reflected from the imaging light source, collected by the camera group, is provided according to a preset standard, and to control the light source to supplement light when the light incoming amount is not sufficient.

5. The visualization system of claim 2, wherein the camera group comprises a fluorescence image sensor and a red light image sensor;

the fluorescence image sensor comprises a first sub image sensor, a second sub image sensor, and a third sub image sensor, which are configured to optionally receive light with different wavelengths, the first sub image sensor receives blue light, the second sub image sensor receives green light and the third sub image sensor receives near infrared light;

the red light image sensor is configured to receive red light.

6. The visualization system in claim 5, wherein the fluorescence image sensor and the red light image sensor are arranged in a same device and are spatially interleaved.

7. The visualization system of claim 2, wherein the camera controller further comprises an image enhancement unit;

the image enhancement unit performs image enhancement on the fluorescence image and the red light image using non-linear histogram equalization, and outputs the fluorescence imaging signal and the red light imaging signal according to an image enhancement result.

8. The visualization system in claim 7, wherein the image enhancement unit includes spatial filtering mechanisms which functions to reduce low spatial frequency signals in the red light signal and increase the high spatial frequency signals in the red light signal.

9. The visualization system of claim 1, wherein a band for the red light emitting from the second light source is in a range of 600 nm to 700 nm.

10. The visualization system of claim 1, wherein a band for the fluorescence excitation light emitting from the first light source is in a range of 780nm to 820 nm, to excite the ICG dye.

11. The visualization system in claim 1, wherein a band for the fluorescence excitation light emitting from the first light source is in a range of 480 nm to 520 nm, to excite the fluorescein dye.

12. The visualization system in claim 1, wherein the receiving end is an endoscope.

13. The visualization system in claim 1, wherein the receiving end is an optical coupling system for use in open surgery when the visualization system is used for open surgery.

* * * * *